(12) United States Patent
Han et al.

(10) Patent No.: US 10,388,420 B2
(45) Date of Patent: Aug. 20, 2019

(54) CONTROLLING ACCELERATOR SYSTEM

(71) Applicant: Shenyang Neusoft Medical Systems Co., Ltd., Shenyang (CN)

(72) Inventors: Donghui Han, Shenyang (CN); Nan Li, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 126 days.

(21) Appl. No.: 15/821,783

(22) Filed: Nov. 23, 2017

(65) Prior Publication Data
US 2018/0144842 A1 May 24, 2018

(30) Foreign Application Priority Data

Nov. 24, 2016 (CN) .......................... 2016 1 1052178

(51) Int. Cl.
*A61N 5/10* (2006.01)
*G21K 1/04* (2006.01)

(52) U.S. Cl.
CPC ............. *G21K 1/046* (2013.01); *A61N 5/107* (2013.01); *A61N 5/1045* (2013.01); *A61N 5/1067* (2013.01); *A61N 5/1036* (2013.01); *A61N 5/1081* (2013.01); *A61N 2005/1074* (2013.01)

(58) Field of Classification Search
None
See application file for complete search history.

(56) References Cited

U.S. PATENT DOCUMENTS

2016/0325117 A1* 11/2016 Arai ..................... A61N 5/1045
2016/0361568 A1* 12/2016 Chappelow .......... A61N 5/1045
2018/0154179 A1* 6/2018 Ollila .................... A61N 5/1036

* cited by examiner

*Primary Examiner* — Hoon K Song
(74) *Attorney, Agent, or Firm* — Kilpatrick Townsend & Stockton LLP

(57) ABSTRACT

An accelerator system is provided. According to an example, the accelerator system includes a ray source, a multi-leaf collimator including leaves, a multi-leaf collimator controller and a leaf position determining device. The multi-leaf collimator controller is configured to control each of the leaves to move according to a predetermined position. The leaf position determining device is configured to obtain a three-dimensional image of the multi-leaf collimator, determine a sub-field shape and a sub-field size of the multi-leaf collimator according to the three-dimensional image, determine an actual position of each of the leaves according to the sub-field shape and the sub-field size and obtain an error value for each of the leaves by comparing the actual position with the predetermined position for each of the leaves. In this way, the error value for each of the leaves may be used to control operation of the accelerator system.

17 Claims, 4 Drawing Sheets

CONTROLLING ACCELERATOR SYSTEM

CROSS REFERENCE TO RELATED APPLICATIONS

This application claims priority to Chinese Patent Application No. 201611052178.6 filed on Nov. 24, 2016, the entire content of which is incorporated herein by reference.

TECHNICAL FIELD

The present disclosure relates to an accelerator system and a method of controlling the accelerator system.

BACKGROUND

A medical electronic linear accelerator may include a multi-leaf collimator (MLC) including a plurality of movable leaves. In a process of tumor radiation therapy, the leaves of the multi-leaf collimator may be formed into a specified shape according to a treatment plan so as to implement conformal radiation therapy or intensity modulated radiation therapy. Thus, tumor treatment effect may be improved and ionizing radiation for a subject may be decreased. In the entire process of tumor radiation therapy, the position of the respective leaves of the multi-leaf collimator shall be accurately controlled. When a leaf position is abnormal, the electronic linear accelerator may be damaged relatively easily, and undesirable ionizing radiation may be brought to the subject.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

DETAILED DESCRIPTION

Figure 1:
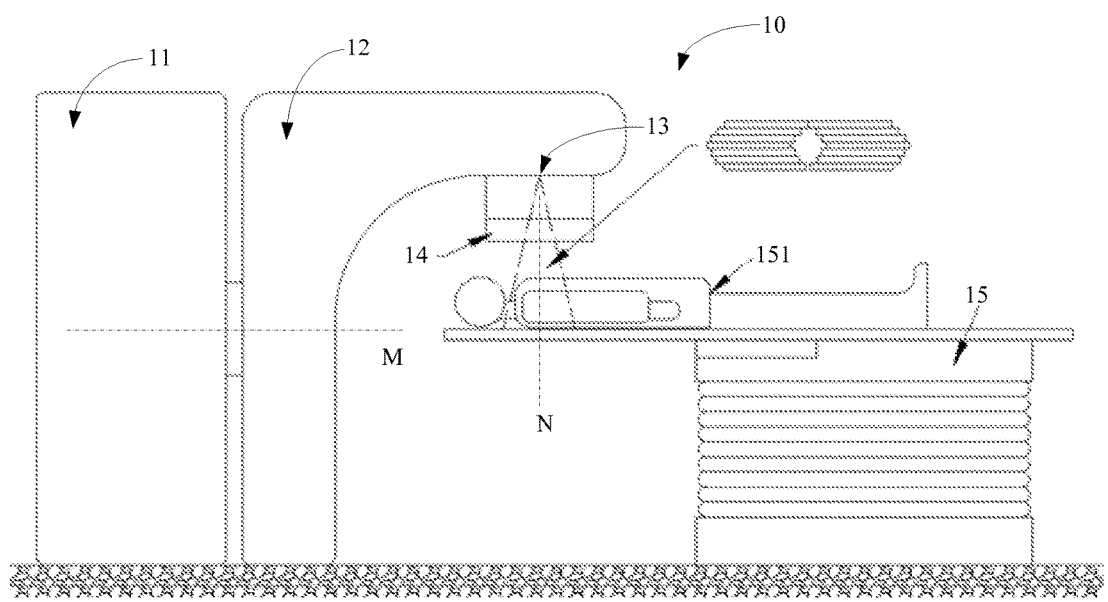
FIG. 1 illustrates a structural diagram of an accelerator system according to an example of the present disclosure.

FIG. 1 illustrates a diagram of an accelerator system 10 according to an example of the present disclosure. In an example, the accelerator system 10 may include a medical accelerator system, such as, an electronic linear accelerator, which is not limited herein. The accelerator system 10 may include a fixing gantry 11, a rotating gantry 12, a radiation head 13, a multi-leaf collimator 14 and a treatment bed 15.

The rotating gantry 12 may be located at one side of the fixing gantry 11. The rotating gantry 12 may be rotated about an axis M of the fixing gantry 11. The radiation head 13 may be connected to a top of the rotating gantry 12 and opposite to the treatment bed 15. The radiation head 13 may include a ray source (not shown in FIG. 1) to emit an imaging ray beam and a treatment ray beam. The imaging ray beam may include an X-ray beam and the treatment ray beam may include a β-ray beam. The multi-leaf collimator 14 may be connected to the radiation head 13. The multi-leaf collimator 14 is a mechanical assembly to produce a conformal radiation field for conformal radiation therapy or intensity modulated radiation therapy. The treatment bed 15 may be used to support a subject 151. The treatment bed 15 may be rotated about an axis N to adjust a position of the subject 151 relative to the radiation head 13, so that the ray beam emitted from the ray source can be irradiated to a particular part of the subject 151.

Figure 2:
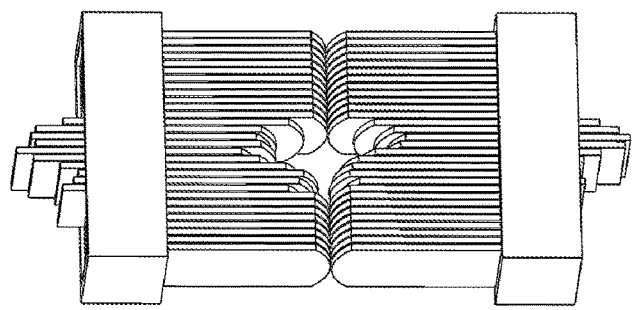
FIG. 2 illustrates a perspective diagram of a multi-leaf collimator according to an example of the present disclosure.

FIG. 2 illustrates a structural diagram of a multi-leaf collimator 14 according to an example of the present disclosure. The multi-leaf collimator 14 includes a fixing support 142 and a plurality of leaves 141 which are disposed on the fixing support 142 and arranged in pairs. Each of the leaves 141 may be driven by a corresponding miniature motor to move. Each of the leaves 141 may be formed into a particular shape at a moment according to a treatment plan (also referred to as a field), for example, an opening, such as a sub-field 143 may be formed in a central region of the multi-leaf collimator 14. The ray beam emitted from the ray source may be irradiated to a part to be examined of the subject after passing through the sub-field 143.

Figure 3:
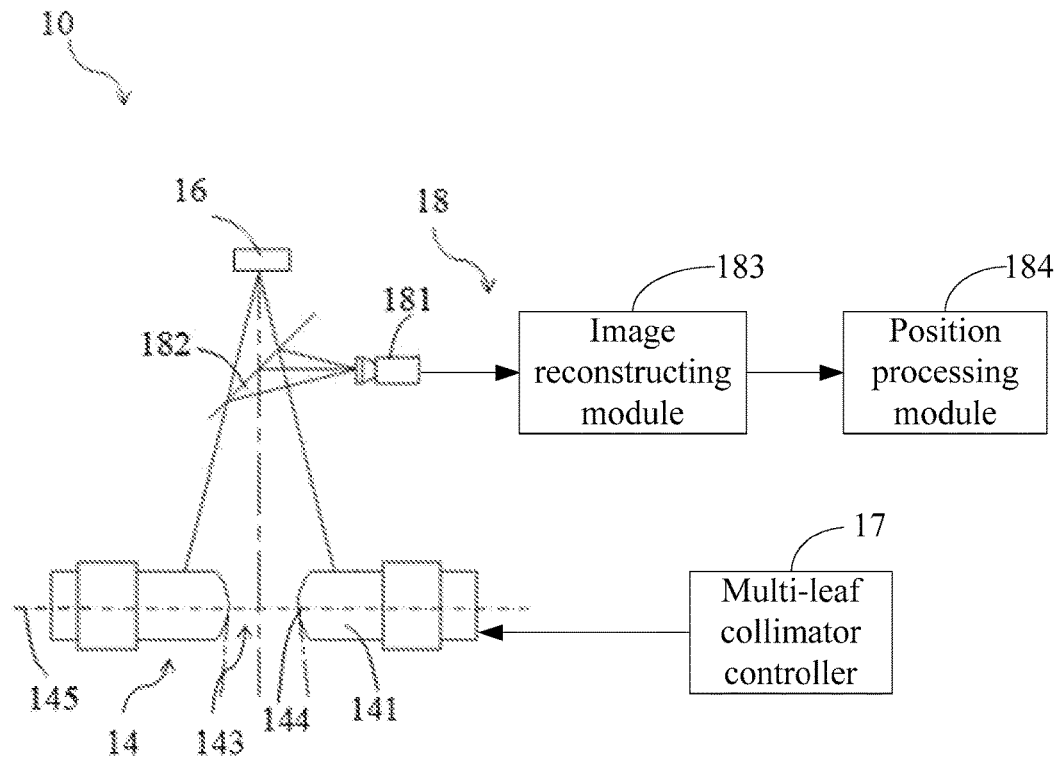
FIG. 3 illustrates a module diagram of an accelerator system according to an example of the present disclosure.

FIG. 3 illustrates a module diagram of an accelerator system 10 according to an example of the present disclosure. The accelerator system 10 includes a ray source 16, a multi-leaf collimator 14, a multi-leaf collimator controller 17 and a leaf position determining device 18. The multi-leaf collimator 14 includes two groups of leaves 141 arranged symmetrically. The multi-leaf collimator controller 17 may be configured to control the respective leaves 141 to move according to a predetermined position of the respective leaves 141. The leaf position determining device 18 may be configured to determine a sub-field shape and a sub-field size of the multi-leaf collimator 14, determine an actual position of the respective leaves 141 according to the sub-field shape and the sub-field size, and obtain an error value for the respective leaves by comparing the actual position with the predetermined position for the respective leaves so as to control operation of the accelerator system 10.

In an example, the leaf position determining device 18 includes a three-dimensional scanner 181, a reflector 182, an image reconstructing module 183 and a position processing module 184.

The three-dimensional scanner 181 may be configured to obtain the three-dimensional image of the multi-leaf collimator 14 by performing a three-dimensional scan on the multi-leaf collimator 14 with an emitted structured light beam.

The reflector 182 may be configured to reflect the structured light beam emitted from the three-dimensional scanner 181 to the multi-leaf collimator 14 to perform the three-dimensional scan.

In an example, the reflector 182 may be located between the ray source 16 and the multi-leaf collimator 14. A reflecting layer of the reflector 182 may face the sub-field 143 of the multi-leaf collimator 14. The three-dimensional scanner 181 may be configured to obtain a three-dimensional coordinate and a reflected light intensity of each of the leaves 141, generate scanning data according to the three-dimensional coordinate and the reflected light intensity of each of the leaves 141, and output the scanning data to the image reconstructing module 183.

The image reconstructing module 183 may be configured to receive the scanning data from the three-dimensional scanner 181 and reconstruct the three-dimensional image of the multi-leaf collimator 14 according to the scanning data.

The position processing module 184 may be configured to determine the sub-field shape and the sub-field size of the multi-leaf collimator 14 according to the three-dimensional image, and determine the actual position of each of the leaves 141 according to the sub-field shape and the sub-field size.

Figure 4:
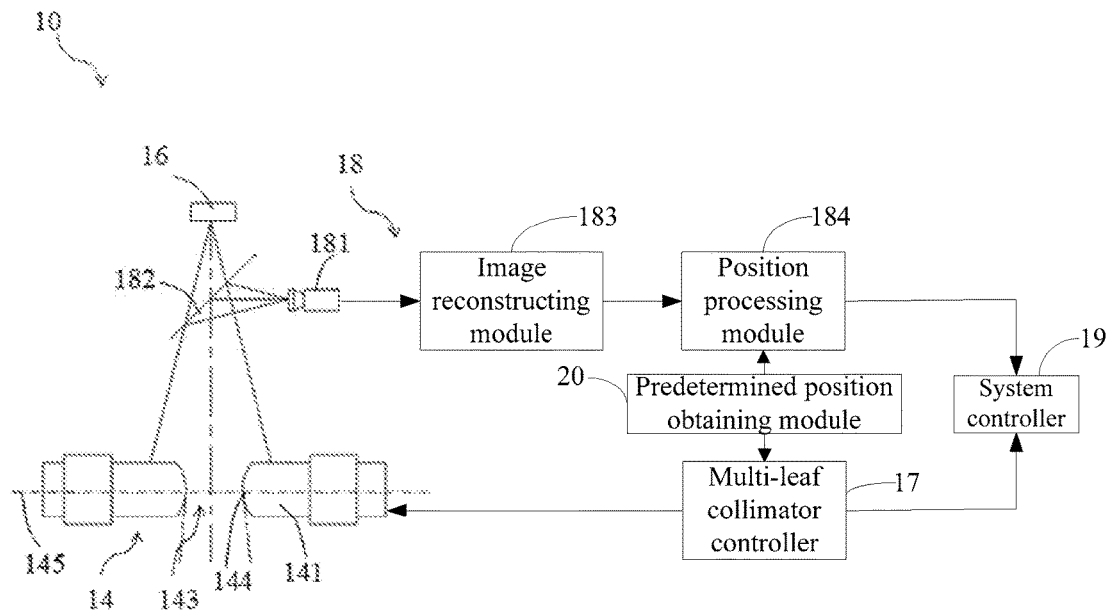
FIG. 4 illustrates a module diagram of an accelerator system according to another example of the present disclosure.

FIG. 4 illustrates a module diagram of an accelerator system 40 according to another example of the present disclosure. The accelerator system 40 shown in FIG. 4 includes all assemblies of the accelerator system 10 shown in FIG. 3. Compared with the accelerator system 10 shown in FIG. 3, the accelerator system 40 shown in FIG. 4 further includes a predetermined position obtaining module 20 and a system controller 19.

In an example, the predetermined position obtaining module 20 may be configured to output the predetermined position of each of the leaves 141 in a sub-field to the multi-leaf collimator controller 17 according to the treatment plan. At this case, the multi-leaf collimator controller 17 may be configured to receive the predetermined position of each of the leaves 141 from the predetermined position obtaining module 20 and control the corresponding motor to drive each of the leaves 141 according to the predetermined position of the each of the leaves 141. In an example, when each of the leaves 141 stops moving, the multi-leaf collimator controller 17 may be configured to notify the system controller 19 that the leaves 141 of the multi-leaf collimator 14 are ready.

The leaf position determining device 18 may be configured to determine the sub-field shape and the sub-field size of the multi-leaf collimator 14, determine the actual position of each of the leaves 141 according to the sub-field shape and the sub-field size, and obtain an error value for each of the leaves 141 by comparing the actual position and the predetermined position for each of the leaves 141, so as to control the operation of the accelerator system 10.

In an example, the leaf position determining device 18 may be configured to obtain the three-dimensional image of the multi-leaf collimator 14, and determine the sub-field shape and the sub-field size according to the three-dimensional image. The leaf position determining device 18 includes a three-dimensional scanner 181, a reflector 182, an image reconstructing module 183 and a position processing module 184.

The three-dimensional scanner 181 may be configured to obtain the three-dimensional image of the multi-leaf collimator 14 by performing a three-dimensional scan on the multi-leaf collimator 14 with an emitted structured light beam. In an example, the three-dimensional scanner 181 may include a three-dimensional laser scanner to emit a laser beam to scan the multi-leaf collimator 14 at a relatively higher scanning speed. In an example, when the system controller 19 receives a notification signal indicating that the respective leaves 141 is ready from the multi-leaf collimator controller 17, it may instruct the three-dimensional scanner 181 to emit the structured light beam for starting scanning the multi-leaf collimator 14.

An area of the structured light beam emitted from the three-dimensional scanner 181 passing through the multi-leaf collimator 14 is as the same as an area of the ray beam emitted from the ray source 16 passing through the multi-leaf collimator 14. In other words, to some extent, the position of the three-dimensional scanner 181 may be equivalent to the position of the ray source 16. The structured light beam emitted from the three-dimensional scanner 181 may be reflected to the multi-leaf collimator 14 by the reflector 182 so that the shape and the size of the sub-field 143 may be obtained. In an example, the three-dimensional scanner 181 may be out of an area in which there is the ray beam emitted from the ray source 16, so as to avoid blocking the ray beam. The reflector 182 may be configured to reflect the structured light beam emitted from the three-dimensional scanner 181 to the multi-leaf collimator 14 to perform a three-dimensional scan. The positions of the three-dimensional scanner 181 and the reflector 182 may be adjusted such that the area of the structured light beam emitted from the three-dimensional scanner 181 passing through the multi-leaf collimator 14 after being reflected by the reflector 182 is the same as the area of the ray beam emitted from the ray source 16 passing through the multi-leaf collimator 14. For example, a propagation path of the structured light beam after being reflected by the reflector 182 may be consistent with that of the ray beam after penetrating the reflector 182.

In an example, the three-dimensional scanner 181 may be parallel to the multi-leaf collimator 14, and the reflector 182 may be at 45 degrees with respect to an axis of the structured light beam emitted from the three-dimensional scanner 181. A distance from the three-dimensional scanner 181 to the reflector 182 may be equal to a distance from the ray source 16 to the reflector 182, and an area on which the structured light beam emitted from the three-dimensional scanner 181 is irradiated to the reflector 182 may be the same as an area through which the ray beam emitted from the ray source 16 penetrates the reflector 182. In this way, the actual position of each of the leaves 141 may be obtained more accurately. In another example, according to actual demands, the three-dimensional scanner 181 may also be placed at an inclination with respect to the multi-leaf collimator 14, and an angle of the reflector 182 relative to the axis of the structured light beam emitted from the three-dimensional scanner 181 may also be adjusted accordingly.

It is noted that the reflecting layer of the reflector 182 may be disposed close to one side of the three-dimensional scanner 181 and face the multi-leaf collimator 14. In this way, the structured light beam emitted from the three-dimensional scanner 181 may be directly reflected by the reflecting layer when arriving at the reflector 182, rather than being refracted when arriving at the reflector 182 in the thickness direction of the reflector 182.

The three-dimensional scanner 181 may be configured to obtain the three coordinate and the reflected light intensity of each of the leaves 141, generate scanning data according to the three coordinate and the reflected light intensity of the each of the leaves 141, and output the scanning data to the image reconstructing module 183. The image reconstructing module 183 may be configured to receive the scanning data from the three-dimensional scanner 181, and reconstruct the three-dimensional image of the multi-leaf collimator 14 according to the scanning data.

Figure 5:
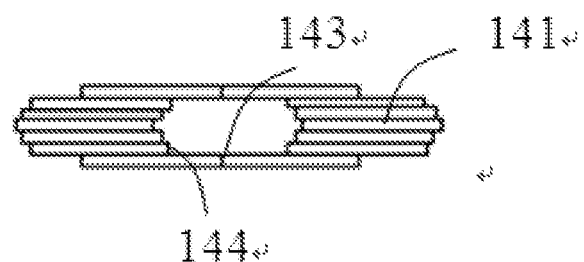
FIG. 5 illustrates a diagram of sectional image of a multi-leaf collimator according to an example of the present disclosure.

The position processing module 184 may be configured to determine the sub-field shape and the sub-field size shown by the multi-leaf collimator 14 according to the three-dimensional image. For example, the position processing module 184 may be configured to obtain a sectional image of the multi-leaf collimator 14 in a cross-sectional direction of the multi-leaf collimator 14 according to the three-dimensional image of the multi-leaf collimator 14. In an example, as shown in FIG. 5, the position processing module 184 may be configured to generate the sectional image of the multi-leaf collimator 14 in the cross sectional direction along an axis 145 of each of the leaves 141. FIG. 5 illustrates a schematic diagram of a sectional image. The actual multi-leaf collimator 14 may include more than one hundred leaves. The sectional image may show each of the leaves 141 and the sub-field 143 of the multi-leaf collimator 14. A tip 144 of each of the leaves 141 is shown in the sectional image, and the tip 144 of the leaves 141 may be formed into an edge contour of the sub-field 143, e.g. the sub-field shape. In another example, the position processing module 184 may be configured to generate the sectional image of the multi-leaf collimator 14 on a cross section that is parallel to the axis 145 and below the axis 145 (e.g., in the direction away from the ray source 16).

Figure 6:
FIG. 6 illustrates a diagram of a sub-field shape obtained from the sectional image shown in FIG. 5.

The position processing module 184 may be further configured to determine the sub-field shape and the sub-field size from the sectional image. FIG. 6 illustrates a sub-field shape obtained from the sectional image shown in FIG. 5. The sub-field shape is a shape of an actual sub-field formed by each of the leaves 141 after being actually moved.

The position processing module 184 may be configured to determine the actual position of each of the leaves 141 according to the sub-field shape and the sub-field size. The position of the tip 144 of each of the leaves 141, e.g., a position to which each of the leaves 141 is controlled by the multi-leaf collimator controller 17 to actually move may be determined according to the sub-field shape and the sub-field size. The position of each of the leaves 141 may be accurately and directly determined according to the actual sub-field shape.

The position processing module 184 may be further configured to obtain an error value for each of the leaves 141 by comparing the actual position with the predetermined position for each of the leaves 141 to control the operation of the accelerator system 10. The position processing module 184 may be further configured to obtain the predetermined position of each of the leaves 141 from the predetermined position obtaining module 20, and determine the error value for each of the leaves 141 between the actual position and the corresponding predetermined position for each of the leaves 141. If the error value for each of the leaves 141 is within a threshold range, e.g., the error value corresponding to each of the leaves 141 is no greater than an error threshold, such as, 1 mm, the accelerator system 10 may be operated normally and proceed with treatment. In an example, the position processing module 184 may be configured to transmit instructions indicating that the position of each of the leaves 141 are normal to the system controller 19, and the system controller 19 may be configured to control the accelerator system 10 to operate normally according to the instructions. If the error value for any one of the leaves 141 is out of the threshold range, e.g., at least one error value is greater than the threshold range, the accelerator system 10 may be stopped to terminate the treatment. In an example, the position processing module 184 may be configured to transmit instructions indicating the positions of the leaves 141 are abnormal to the system controller 19, and the system controller 19 may be configured to control the accelerator system 10 to stop according to the instructions. The position processing module 184 may be configured to determine the at least one abnormal error value and the respective leaves 141 corresponding to the at least one abnormal error value for eliminating a failure. In this way, the subject may be prevented from being injured by the undesirable ionizing radiation caused by the failure of the multi-leaf collimator 14.

The image reconstructing module 183, the position processing module 184, the predetermined position obtaining module 20, the multi-leaf collimator controller 17 and/or the system controller 19 of the accelerator system 10 may be implemented by software, hardware or a combination thereof. The image reconstructing module 183, the position processing module 184, the predetermined position obtaining module 20, the multi-leaf collimator controller 17 and/or the system controller 19 may be a plurality of independent modules and may also be integrated into one module, for example, functions corresponding to these modules may be implemented on a control software platform of the accelerator system. The accelerator system 10 may further include other assemblies not shown in the drawings, such as a memory, a display and an input device.

The system embodiments described above are merely illustrative, where the modules described as separate members may be or not be physically separated, and the members displayed as modules may be or not be physical modules, i.e., may be located in one place, or may be distributed to a plurality of network modules. Part or all of the modules may be selected according to actual requirements to implement the objectives of the solutions in the embodiments. Those of ordinary skill in the art may understand and carry out them without creative work.

Figure 7:
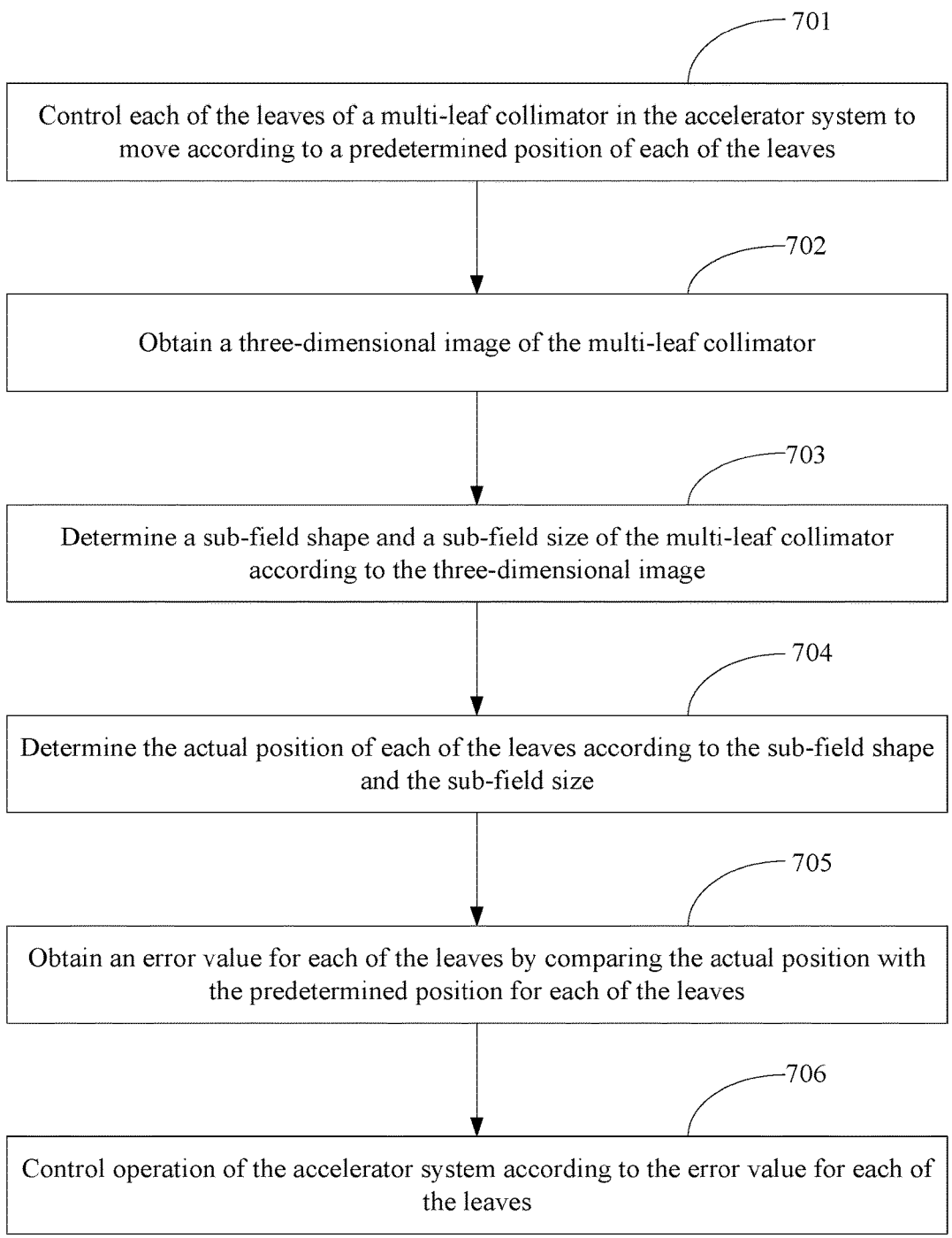
FIG. 7 illustrates a flow diagram of a method of controlling an accelerator system according to an example of the present disclosure.

FIG. 7 illustrates a flow diagram of a method 70 of controlling an accelerator system according to an example of the present disclosure. The flow includes the following blocks 701-706.

At block 701, each of the leaves of a multi-leaf collimator in the accelerator system is controlled to move according to a predetermined position of each of the leaves.

At block 702, a three-dimensional image of the multi-leaf collimator is obtained.

At block 703, a sub-field shape and a sub-field size of the multi-leaf collimator are determined according to the three-dimensional image.

At block 704, the actual position of each of the leaves is determined according to the sub-field shape and the sub-field size.

At block 705, an error value for each of the leaves is obtained by comparing the actual position with the predetermined position for each of the leaves.

At block 706, operation of the accelerator system is controlled according to the error value for each of the leaves.

In an example, obtaining the three-dimensional image of the multi-leaf collimator may include obtaining the three-dimensional image of the multi-leaf collimator with a leaf position determining device in the accelerator system, and the leaf position determining device comprises a three-dimensional scanner and a reflector.

In an example, obtaining the three-dimensional image of the multi-leaf collimator may include controlling the three-dimensional scanner to emit a structured light beam, reflecting the structured light beam to the multi-leaf collimator by the reflector, collect reflected light information from each of the leaves of the multi-leaf collimator, where the reflected light information comprises a three-dimensional coordinate and a reflected light intensity of each of the leaves of the multi-leaf collimator, and reconstruct the three-dimensional image of the multi-leaf collimator according to the reflected light information.

In an example, controlling the operation of the accelerator system according to the error value for each of the leaves may include continuously operating the accelerator system when the error value for each of the leaves is within a preset threshold range, and stopping the accelerator system when the error value for any one of the leaves is out of the threshold range.

In an example, a distance for the structured light beam travelling to the reflector is equal to a distance for a ray beam emitted by a ray source in the accelerator system travelling to the reflector. An area on which the structured light beam is irradiated to the reflector is the same as an area through which the ray beam penetrates the reflector.

In an example, the reflector is located between the ray source and the multi-leaf collimator. At this case, a reflecting layer of the reflector faces the multi-leaf collimator.

In an example, the three-dimensional scanner is parallel to the multi-leaf collimator. The reflector is at 45 degrees with respect to an axis of the structured light beam.

In an example, the flow further includes adjusting the position of the three-dimensional scanner such that an area of the structured light beam passing through the multi-leaf collimator is the same as an area of a ray beam emitted from the ray source passing through the multi-leaf collimator.

In an example, determining the sub-field shape and the sub-field size of the multi-leaf collimator according to the three-dimensional image may include obtaining a sectional image of the multi-leaf collimator in a cross sectional direction of the multi-leaf collimator according to the three-dimensional image, and determining the sub-field shape and the sub-field size according to the sectional image.

The actual position of each of the leaves may be directly determined according to the sub-field shape and the sub-field size by this method. The method can be relatively stable and reliable. The implementation process of the above blocks may be referred to the implementation process corresponding to the above accelerator system 10, which is not described redundantly. Since method embodiments substantially correspond to the system embodiments, reference may be made to a partial description of the system embodiments for related parts.

The foregoing description is merely illustrative of embodiments of the present disclosure but not intended to limit the present disclosure, and any modifications, equivalent substitutions, adaptations thereof made within the spirit and principles of the disclosure shall be encompassed in the scope of protection of the present disclosure.

The invention claimed is:

1. An accelerator system, comprising:
a ray source;
a multi-leaf collimator comprising:
a plurality of leaves;
a multi-leaf collimator controller configured to control each of the plurality of leaves to move according to a predetermined position of each of the plurality of leaves; and
a leaf position determining device which is configured to:
obtain a three-dimensional image of the multi-leaf collimator;
determine a sub-field shape and a sub-field size of the multi-leaf collimator according to the three-dimensional image;
determine an actual position of each of the plurality of leaves according to the sub-field shape and the sub-field size; and
obtain an error value for each of the plurality of leaves by comparing the actual position with the predetermined position for each of the plurality of leaves, wherein the error value for each of the plurality of leaves is used to control operation of the accelerator system.

2. The accelerator system according to claim 1, wherein the leaf position determining device is further configured to:
obtain a sectional image of the multi-leaf collimator in a cross sectional direction of the multi-leaf collimator with the three-dimensional image; and
determine the sub-field shape and the sub-field size according to the sectional image.

3. The accelerator system according to claim 1, wherein the leaf position determining device comprises a three-dimensional scanner configured to obtain the three-dimensional image of the multi-leaf collimator by performing a three-dimensional scan on the multi-leaf collimator with an emitted structured light beam.

4. The accelerator system according to claim 3, wherein the leaf position determining device further comprises a reflector configured to reflect the structured light beam to the multi-leaf collimator for performing the three-dimensional scan.

5. The accelerator system according to claim 4, wherein an area of the structured light beam passing through the multi-leaf collimator is the same as an area of a ray beam emitted from the ray source passing through the multi-leaf collimator.

6. The accelerator system according to claim 4, wherein,
the reflector is located between the ray source and the multi-leaf collimator; and
a reflecting layer of the reflector faces the multi-leaf collimator.

7. The accelerator system according to claim 6, wherein,
a distance for the structured light beam travelling to the reflector is equal to a distance for the ray beam emitted from the ray source travelling to the reflector; and
an area on which the structured light beam is irradiated to the reflector is the same as an area through which the ray beam penetrates the reflector.

8. The accelerator system according to claim 7, wherein,
the three-dimensional scanner is parallel to the multi-leaf collimator; and
the reflector is at 45 degrees with respect to an axis of the structured light beam.

9. A method of controlling an accelerator system, comprising:
controlling each of leaves of a multi-leaf collimator in the accelerator system to move according to a predetermined position of each of the leaves;
obtaining a three-dimensional image of the multi-leaf collimator;

determining a sub-field shape and a sub-field size of the multi-leaf collimator according to the three-dimensional image;

determining an actual position of each of the leaves of the multi-leaf collimator according to the sub-field shape and the sub-field size;

obtaining an error value for each of the leaves according to the actual position and the predetermined position for each of the leaves; and controlling operation of the accelerator system according to the error value for each of the leaves.

10. The method according to claim 9, wherein obtaining the three-dimensional image of the multi-leaf collimator comprises:

obtaining the three-dimensional image of the multi-leaf collimator with a leaf position determining device in the accelerator system, wherein the leaf position determining device comprises a three-dimensional scanner and a reflector.

11. The method according to claim 10, wherein obtaining the three-dimensional image of the multi-leaf collimator comprises:

controlling the three-dimensional scanner to emit a structured light beam, reflecting the structured light beam to the multi-leaf collimator by the reflector;

collecting reflected light information from each of the leaves of the multi-leaf collimator, wherein the reflected light information comprises a three-dimensional coordinate and a reflected light intensity of each of the leaves of the multi-leaf collimator; and reconstructing the three-dimensional image of the multi-leaf collimator according to the reflected light information.

12. The method according to claim 9, wherein controlling the operation of the accelerator system according to the error value for each of the leaves comprises:

continuously operating the accelerator system when the error value for each of the leaves is within a preset threshold range; and stopping the accelerator system when the error value for any one of the leaves is out of the threshold range.

13. The method according to claim 11, wherein, a distance for the structured light beam travelling to the reflector is equal to a distance for a ray beam emitted by a ray source in the accelerator system travelling to the reflector; and an area on which the structured light beam is irradiated to the reflector is the same as an area through which the ray beam penetrates the reflector.

14. The method according to claim 13, wherein, the reflector is located between the ray source and the multi-leaf collimator; and a reflecting layer of the reflector faces the multi-leaf collimator.

15. The method according to claim 11, wherein, the three-dimensional scanner is parallel to the multi-leaf collimator; and the reflector is at 45 degrees with respect to an axis of the structured light beam.

16. The method according to claim 11, further comprising:

adjusting the position of the three-dimensional scanner such that an area of the structured light beam passing through the multi-leaf collimator is the same as an area of a ray beam emitted from the ray source passing through the multi-leaf collimator.

17. The method according to claim 9, wherein determining the sub-field shape and the sub-field size of the multi-leaf collimator according to the three-dimensional image comprises:

obtaining a sectional image of the multi-leaf collimator in a cross sectional direction of the multi-leaf collimator according to the three-dimensional image; and determining the sub-field shape and the sub-field size according to the sectional image.

* * * * *